(12) United States Patent
Sabater-Lüntzel et al.

(10) Patent No.: US 6,306,451 B1
(45) Date of Patent: Oct. 23, 2001

(54) FRAGRANCE AND FLAVOR MATERIAL

(75) Inventors: Christopher Sabater-Lüntzel, Höxter-Ottbergen; Sabine Widder, Holzminden; Wilhelm Pickenhagen, Höxter; Tobias Vössing, Beverungen, all of (DE)

(73) Assignee: DRAGOCO Gerberding & Co. AG (DE)

( * ) Notice: Subject to any disclaimer, the term of this patent is extended or adjusted under 35 U.S.C. 154(b) by 0 days.

(21) Appl. No.: 09/378,400

(22) Filed: Aug. 20, 1999

(30) Foreign Application Priority Data

Aug. 20, 1998 (DE) .................................. 198 37 703

(51) Int. Cl.[7] ............................. A23L 1/22; C07C 315/00
(52) U.S. Cl. .................. 426/535; 426/534; 426/650; 568/18
(58) Field of Search ................................... 426/534, 535, 426/650; 568/18, 61, 62

(56) References Cited

U.S. PATENT DOCUMENTS

| 3,892,878 | 7/1975 | Wilson et al. | 426/534 |
| 5,493,060 | * 2/1996 | Rubino et al. | 568/721 |

OTHER PUBLICATIONS

Pickenhagen, "Enantioselective Synthesis of (+)–and (–)–cis–2–methyl–4–propyl–1,3–oxathiane and their Olfactive Properties", Helvetica Chemica Acta vol. 67 (1984).

* cited by examiner

Primary Examiner—Leslie Wong
(74) Attorney, Agent, or Firm—Pendorf & Cutliff

(57) ABSTRACT

Described is a 2-mercapto-2-methyl-pentan-1-ol compound, which is especially useful as fragrance or flavor compound. For the production of 2-mercapto-2-methyl-pentan-1-ol, 2,3-epithio-2-methyl-pentan-1-ol can be reduced. The described compound can provide foodstuffs an interesting, gustatory and fragrant note.

7 Claims, 4 Drawing Sheets

FRAGRANCE AND FLAVOR MATERIAL

BACKGROUND OF THE INVENTION

1. Field of the Invention

The invention relates to a novel fragrance and flavor material and to a process for the preparation of this novel material.

2. Description of the Related Art

Foods are nowadays frequently flavored. This is because most consumers in modern industrialized societies expect a wide range of tasty foods at reasonable prices. The tastiness of food is very important since it generally brings about good digestibility. The flavoring industry has already made available a large number of flavors in order to make food available to and tasty for a large section of the population.

Flavor materials are used in order (a) to impart a taste note to food products which do not have their own taste, or (b) to compensate for losses in flavor which occur, for example, during the preparation process of a foodstuff.

SUMMARY OF THE INVENTION

The object of the present invention was to give a novel material for the flavoring of food (below also called "flavor material" for short).

According to the invention, the compound 2-mercapto-2-methylpentan-1-ol, the structural formula for which is given below, is given as flavor material.

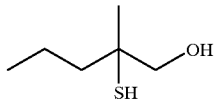

This is because, surprisingly, it has been found that this newly synthesized compound is highly suitable for imparting an interesting olfactory and gustatory note to foods. Because the compound according to the invention has a very high odoriferous and gustatory intensity, it can be used in large dilution; the person skilled in the art will adapt the exact concentration or amount for the flavoring of a foodstuff in the usual manner to the respective wishes and requirements of the individual case.

Moreover, the compound according to the invention is also suitable for use as fragrance material, in particular as fragrance material in the perfume industry; it generally has a particularly low odor threshold value, which is proving advantageous since even small amounts of a compound according to the invention suffice to achieve a desired odor.

In addition to the compound according to the invention itself, the invention also relates to a process for its preparation.

In this process according to the invention for the preparation of 2-mercapto-2-methylpentan-1-ol, 2,3-epithio-2-methylpentan-1-ol is subjected to a reduction treatment.

According to the preferred field of use for the compound according to the invention, the invention also relates to fragrance or flavor material formulations which comprise the compound according to the invention.

And finally, the invention also relates to flavored foods with a content of 2-mercapto-2-methylpentan-1-ol, and to the use of this compound as fragrance and flavor material.

BRIEF DESCRIPTION OF THE DRAWINGS

For a fuller understanding of the nature and objects of the present invention reference should be made by the following detailed description taken in with the accompanying drawings in which.

DETAILED DESCRIPTION OF THE INVENTION

Figure 1:
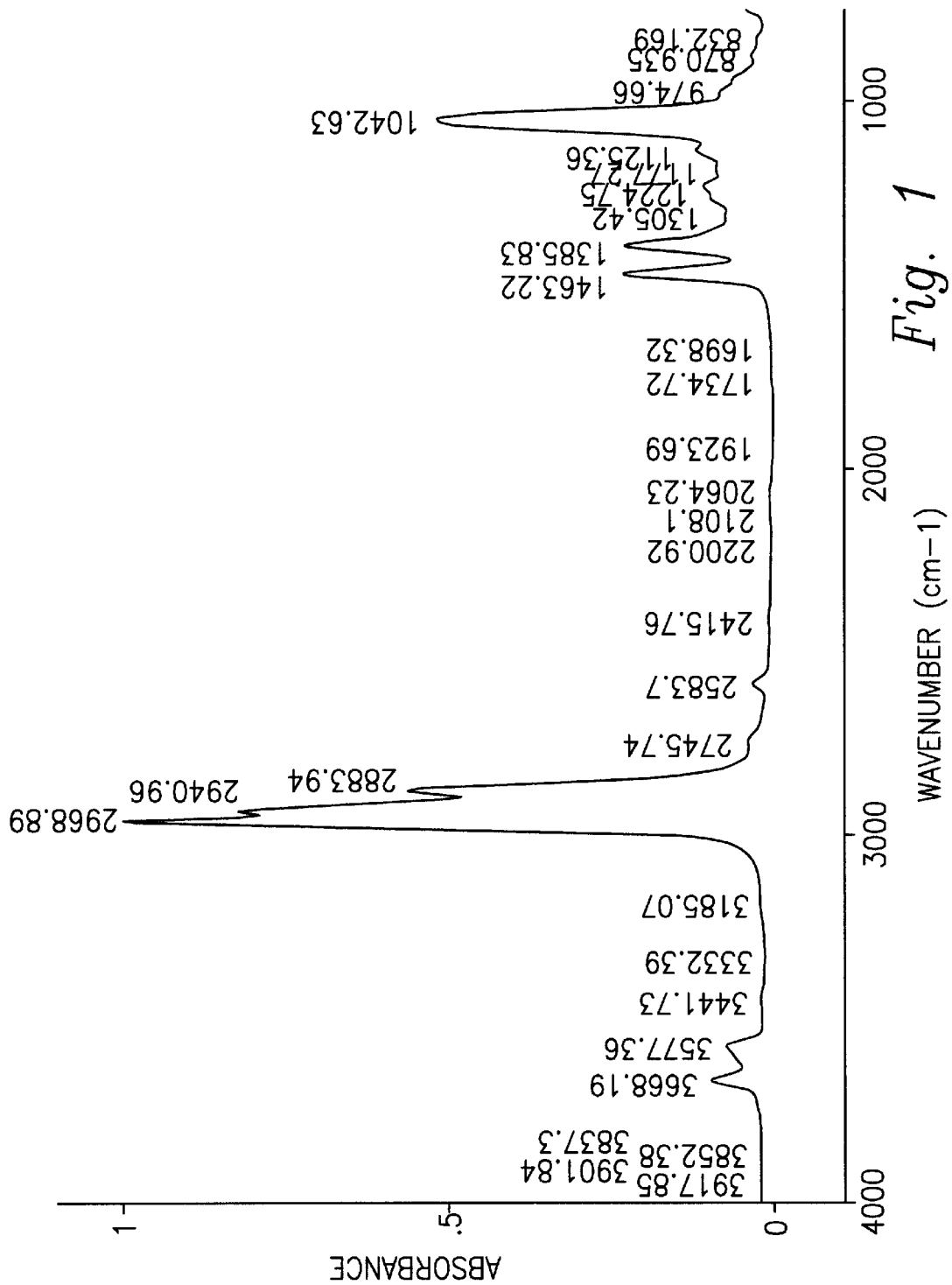
FIGS. 1–4 are IR and MNR spectrum for 2-mercapto-2-methyl-pentan-1-ol produced in Example 1.

The invention is described in more detail below by reference to examples:

EXAMPLE 1

Preparation of 2-mercapto-2-methylpentan-1-ol 1.1. Preparation of trans-2,3-epoxy-2-methylpentan-1-ol by epoxidation of trans-2-methyl-2-penten-1-ol (CAS No. [16958-19-3])

20 g (0.2 mol) of 2-methyl-2-penten-1-ol (readily obtainable from the lithium aluminum hydride reduction of the commercially available 2-methyl-2-pentenal) are dissolved in 200 ml of methylene chloride and cooled to 0° C. in an ice bath. 59 g (0.36 mol) of solid m-chloroperbenzoic acid (about 70% strength) are then added in small portions, and the mixture is then stirred for a further 2 h at 0° C. and overnight at room temperature. 8 g of calcium hydroxide are then added and the mixture is stirred for 1 h. The mixture is filtered, and the filter residue is washed thoroughly with diethyl ether. The combined organic phases are washed once with 50 ml of 5% strength sodium carbonate solution and once with 50 ml of saturated sodium chloride solution, dried over sodium sulfate and filtered, and the solvent is carefully stripped off under partial vacuum. Yield 65%. The resulting epoxy alcohol is used in the next reaction without further purification. Yield 15.08 g (65%).

trans-2,3-Epoxy-2-methylpentan-1-ol

MS (EI, 70 eV): no $M^+$, 74 (15), 59 (60), 58 (99), 57 (58), 43 (100), 41 (29), 39 (21)

1.2. Preparation of 2,3-epithio-2-methylpentan-1-ol from trans-2,3-epoxy-2-methylpentan-1-ol A dry 250 ml stirred apparatus is charged, under a nitrogen atmosphere, with 1.57 g (20.6 mmol) of thiourea, 100 ml of tetrahydrofuran and 2 g (17 mmol) of the epoxy alcohol trans-2,3-epoxy-2-methylpentan-1-ol synthesized as in 1.1. 5.87 g (20.6 mmol) of titanium tetraisopropoxide is slowly added dropwise thereto at room temperature. After the thiourea has dissolved, the mixture is stirred for a further 2 h at room temperature. 70 ml of diethyl ether and 35 ml of saturated sodium hydrogencarbonate solution are then added, and the mixture is stirred for a further 1 h. The suspension is filtered with suction, and the filter cake is washed with 3×30 ml of diethyl ether and then with 2×30 ml of methylene chloride. The combined organic phases are washed with 2×70 ml of water and with 1×70 ml of saturated sodium chloride solution, dried over sodium sulfate and filtered, and the solvent is carefully stripped off under partial vacuum. The product is used in the next reaction without further purification. Yield: 1.08 g (75%).

2,3-Epithio-2-methylpentan-1-ol

MS (EI, 70 eV): 132 ($M^+$79), 101 (12), 99 (59), 98 (10), 85 (14), 81 (17), 75 (20), 74 (50), 73 (15), 71 (33), 70 (22), 69 (21), 67 (19), 61 (20), 59 (100), 58 (31), 57 (25), 55 (23), 53 (14), 47 (14), 45 (28), 43 (54), 41 (71), 39 (36)

1.3. Reductive opening of the thiirane 2,3-epithio-2-methylpentan-1-ol to give 2-mercapto-2-methyl-pentan-1-ol A solution of the thiirane as synthesized in 1.2. (3.87 g, 29.3 mmol) in 30 ml of diethyl ether is slowly added dropwise, under a nitrogen atmosphere and at −20° C., to a solution of 6.22 g of sodium bis(2-methoxyethoxy) aluminum dihydride (65% by weight in toluene, 30.8 mmol) and 30 ml of diethyl ether. Following the dropwise addition, the mixture is then stirred for a further 5 h at room temperature. At 0° C., the mixture is very carefully hydrolyzed firstly using 5 ml of water and then using 10% strength sulfuric acid. The phases are separated, and the aqueous phase is extracted once with 20 ml of diethyl ether. The combined organic phases are washed with 30 ml saturated sodium hydrogencarbonate solution, dried over sodium sulfate and filtered, and the solvent is carefully stripped off under partial vacuum to give a crude product, which is purified by column chromatography (79% hexane/14% methylene chloride/7% diethyl ether). Yield: 380 mg (9.7%)

Spectroscopic data for 2-mercapto-2-methylpentan-1-ol:

IR (gas phase): 3668 (w), 3577 (w), 2968 (s), 2584 (w), 2941 (s), 2884 (m), 1463 (m), 1386 (m), 1043 (m)
w=weak, m=medium, s=strong bands $^1$H-NMR (300 MHz, d$_6$-benzene, 300 K, internal standard: TMS): δ=0.8 (triplet-like multiplet, 3H, —CH$_3$), 1.1 (s, 3H, —CH$_3$), 1.2–1.4 (m, 5H, 2 times CH$_2$ and SH), 2.0 (brs, 1H, OH), 3.2 (brs, 2H, CH$_2$)
Multiplicities: s=singlet, brs=broad singlet, m=multiplet $^{13}$C-NMR (75 MHz, d$_6$-benzene, 300 K, internal standard: TMS): δ=72.2, 50.1, 42.9, 25.9, 18.0, 14.6

MS (EI, 70 eV): 134 (M$^+$, 10), 116 (0.1), 103 (100), 102 (80), 91 (8), 83 (25), 73 (18), 69 (74), 61 (95), 59 (40), 55 (38), 45 (36), 43 (20), 41 (60)

Figure 2:
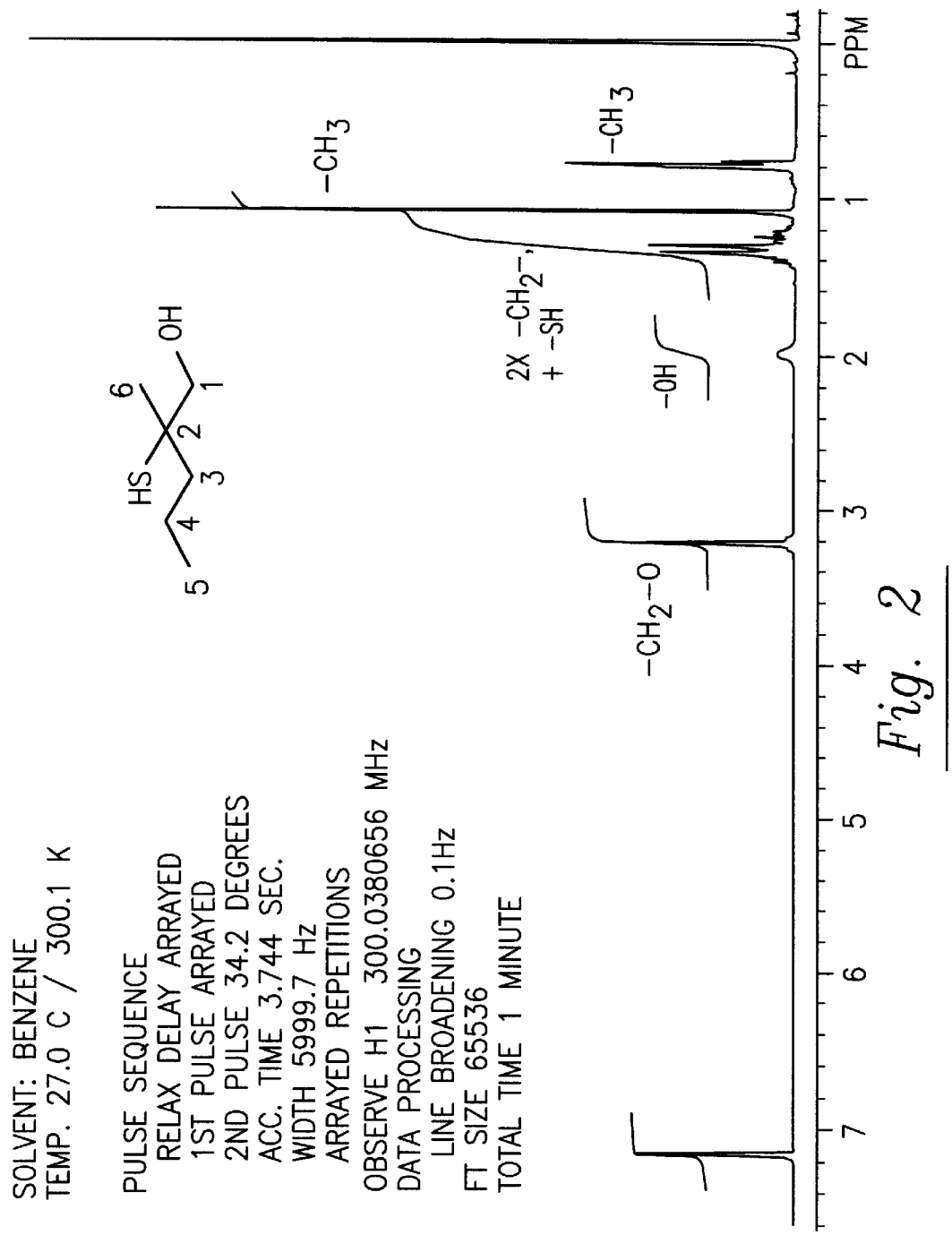
Figure 3:
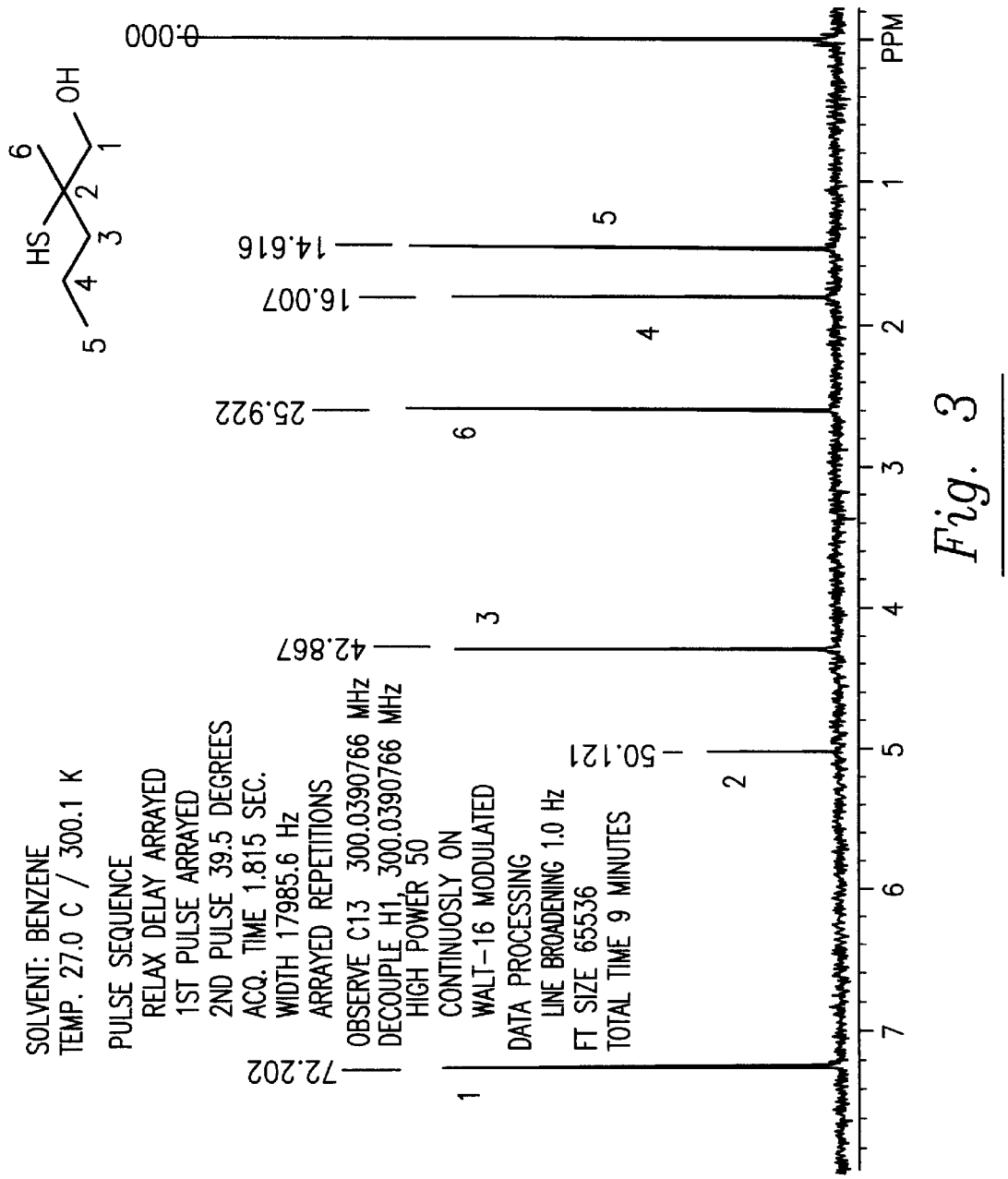
Figure 4:
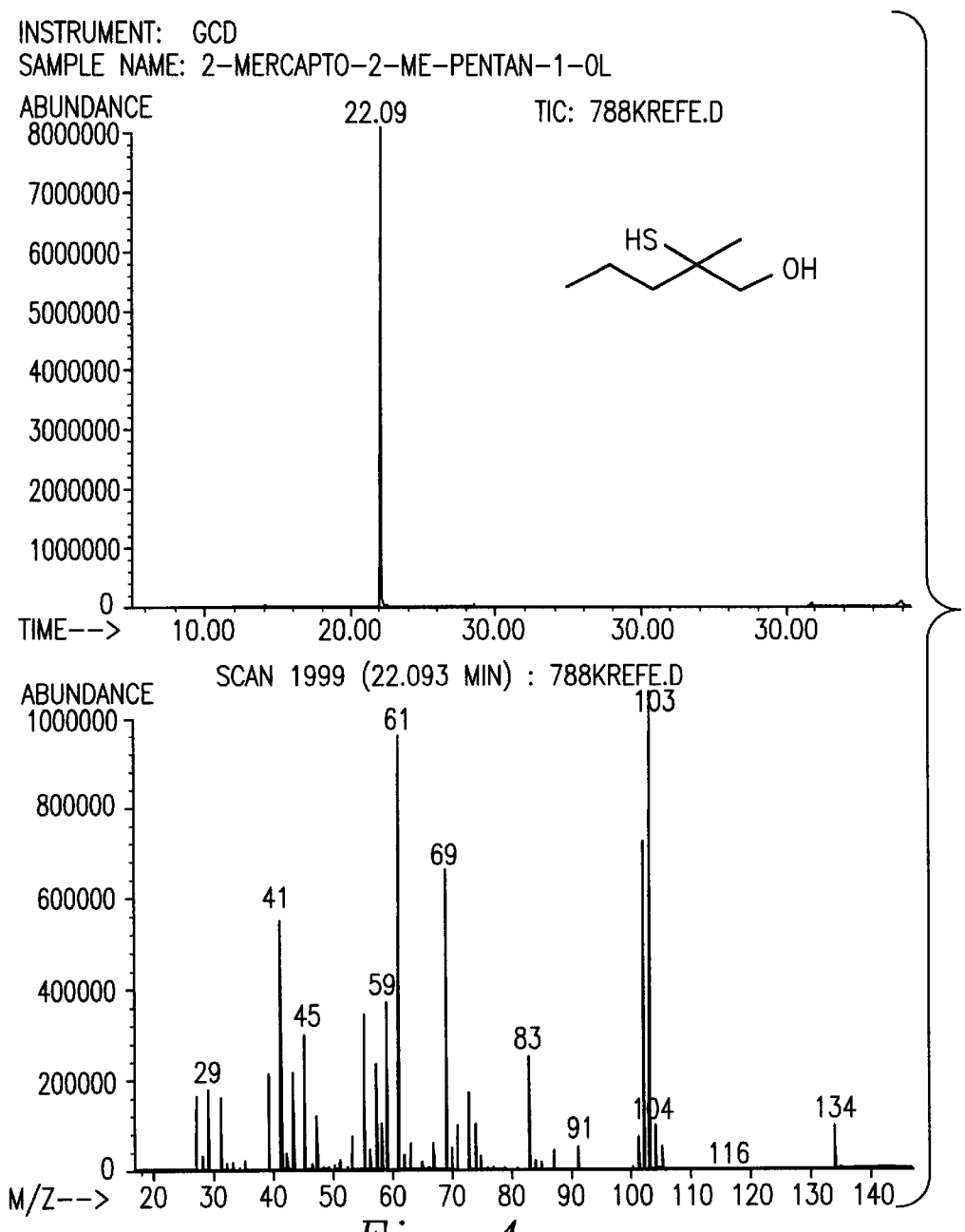

The attached spectrum for 2-mercapto-2-methyl-pentan-1-ol correspond to this spectroscopic data. These show:
FIG. 1 IR spectrum
FIG. 2 $^1$H-NMR spectrum
FIG. 3 $^{13}$C-NMR spectrum
FIG. 4 mass spectrum

EXAMPLE 2

Sensory testing of 2-mercapto-2-methyl-pentan-1-ol
Description of Odor
  burnt plastic, rubber, pungent, grapefruit, blackcurrant, strong
Description of Taste
  sulfurous, aldehydic, tropical fruit, pungent, rubber, grapefruit
Odor Threshold Value
  0.1 ppb (0.1 μg/l of water)

What is claimed is:
1. 2-mercapto-2-methyl-pentan-1-ol.
2. A fragrance or flavor material containing 2-mercapto-2-methyl-pentan-1-ol.
3. A fragrance or flavor material as in claim 2, wherein said 2-mercapto-2-methyl-pentan-1-ol is present in an organoleptically effective amount.
4. A process for production of 2-mercapto-2-methyl-pentan-1-ol, comprising reducing 2,3-epithio-2-methyl-pentan-ol.
5. A process for organoleptically modifying a composition, comprising adding to said composition 2-mercapto-2-methyl-pentan-1-ol as fragrance or flavor agent.
6. A process for organoleptically modifying a composition as in claim 5, wherein said 2-mercapto-2-methyl-pentan-1-ol is added in an organoleptically effective amount.
7. A foodstuff comprising 2-mercapto-2-methyl-pentan-1-ol.

* * * * *